United States Patent [19]
Yoon

[11] Patent Number: 5,827,315
[45] Date of Patent: Oct. 27, 1998

[54] SAFETY PENETRATING INSTRUMENT WITH PENETRATING MEMBER PROTECTED AFTER PENETRATION TO PREDETERMINED DEPTH

[76] Inventor: InBae Yoon, 2101 Highland Ridge Dr., Phoenix, Md. 21131

[21] Appl. No.: 177,616

[22] Filed: Jan. 4, 1994

[51] Int. Cl.⁶ .................................................. A61M 5/20
[52] U.S. Cl. ......................................... 606/185; 604/157
[58] Field of Search ................................... 606/184, 185, 606/181–182; 604/164, 165, 157, 158, 159

[56] References Cited

U.S. PATENT DOCUMENTS

| | | |
|---|---|---|
| Re. 32,922 | 5/1989 | Levin et al. . |
| 1,527,291 | 2/1925 | Zorraquin ................................ 604/158 |
| 2,496,111 | 1/1950 | Turkel . |
| 2,623,521 | 12/1952 | Shaw ....................................... 604/158 |
| 2,630,803 | 3/1953 | Baran . |
| 4,254,762 | 3/1981 | Yoon . |
| 4,345,589 | 8/1982 | Hiltebrandt . |
| 4,442,836 | 4/1984 | Meinecke et al. .................. 604/157 X |
| 4,488,545 | 12/1984 | Shen ..................................... 604/165 X |
| 4,503,856 | 3/1985 | Cornell et al. . |
| 4,535,773 | 8/1985 | Yoon . |
| 4,559,041 | 12/1985 | Razi ..................................... 604/164 X |
| 4,601,710 | 7/1986 | Moll . |
| 4,627,841 | 12/1986 | Dorr . |
| 4,654,030 | 3/1987 | Moll et al. . |
| 4,670,008 | 6/1987 | Von Albertini . |
| 4,677,979 | 7/1987 | Burns . |
| 4,747,831 | 5/1988 | Kulli . |
| 4,817,603 | 4/1989 | Turner et al. . |
| 4,820,275 | 4/1989 | Haber et al. . |
| 4,869,717 | 9/1989 | Adair . |
| 4,889,117 | 12/1989 | Stevens . |
| 4,900,307 | 2/1990 | Kulli . |
| 4,902,280 | 2/1990 | Lander . |
| 4,906,236 | 3/1990 | Alberts et al. ....................... 604/164 X |
| 4,931,042 | 6/1990 | Holmes et al. . |
| 4,943,280 | 7/1990 | Lander . |
| 4,946,446 | 8/1990 | Vadher . |
| 4,955,870 | 9/1990 | Ridderheim et al. . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |

(List continued on next page.)

FOREIGN PATENT DOCUMENTS

| | | |
|---|---|---|
| 2544262 | 4/1977 | Germany . |
| 1435246 | 11/1988 | Russian Federation . |

*Primary Examiner*—Glenn K. Dawson
*Assistant Examiner*—Nancy Mulcare

[57] ABSTRACT

A safety penetrating instrument for penetrating an anatomical cavity wall to gain access to an anatomical cavity includes a cannula having a distal end for introduction in the anatomical cavity, a penetrating member disposed in the cannula and having a distal end for penetrating the anatomical cavity wall protection means for placing the safety penetrating instrument in a protected state where the penetrating member distal end is protected and not exposed and trigger means proximally movable during penetration of the anatomical cavity wall for triggering the protection means to place the safety penetrating instrument in the protected state upon the trigger means moving a predetermined proximal distance. Where the predetermined proximal distance corresponds to the thickness of the anatomical cavity wall, the safety penetrating instrument will be placed in the protected state upon introduction of the cannula distal end in the anatomical cavity. A method of forming a portal in an anatomical cavity wall includes the steps of penetrating the anatomical cavity wall with a safety penetrating instrument and triggering the safety penetrating instrument to move to a protected state where a penetrating member of the safety penetrating instrument is protected upon movement of a trigger member of the safety penetrating instrument a predetermined proximal distance corresponding to the thickness of the anatomical cavity wall.

27 Claims, 5 Drawing Sheets

U.S. PATENT DOCUMENTS

| | | |
|---|---|---|
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |
| 5,066,288 | 11/1991 | Deniega et al. . |
| 5,104,382 | 4/1992 | Brinkerhoff et al. .................. 604/167 |
| 5,104,383 | 4/1992 | Shichman ................................ 604/165 |
| 5,114,407 | 5/1992 | Burbank ................................. 604/164 |
| 5,116,353 | 5/1992 | Green .................................... 606/184 |
| 5,127,909 | 7/1992 | Shichman ................................ 604/165 |
| 5,129,885 | 7/1992 | Green et al. ........................... 604/164 |
| 5,152,754 | 10/1992 | Plyley et al. ........................... 604/164 |
| 5,158,552 | 10/1992 | Borgia et al. ........................... 604/165 |
| 5,207,647 | 5/1993 | Phelps .................................... 604/158 |
| 5,226,426 | 7/1993 | Yoon ................................. 604/165 X |
| 5,226,891 | 7/1993 | Bushatz et al. ......................... 604/165 |
| 5,290,243 | 3/1994 | Chodorow et al. ..................... 604/165 |
| 5,290,304 | 3/1994 | Storace .................................. 606/184 |
| 5,295,993 | 3/1994 | Green .................................... 606/184 |
| 5,312,354 | 5/1994 | Allen et al. ............................. 604/157 |
| 5,318,580 | 6/1994 | Gresl, Jr. ................................ 606/185 |
| 5,318,585 | 6/1994 | Guy et al. .............................. 606/185 |
| 5,320,610 | 6/1994 | Yoon ...................................... 604/158 |
| 5,324,268 | 6/1994 | Yoon ...................................... 604/158 |

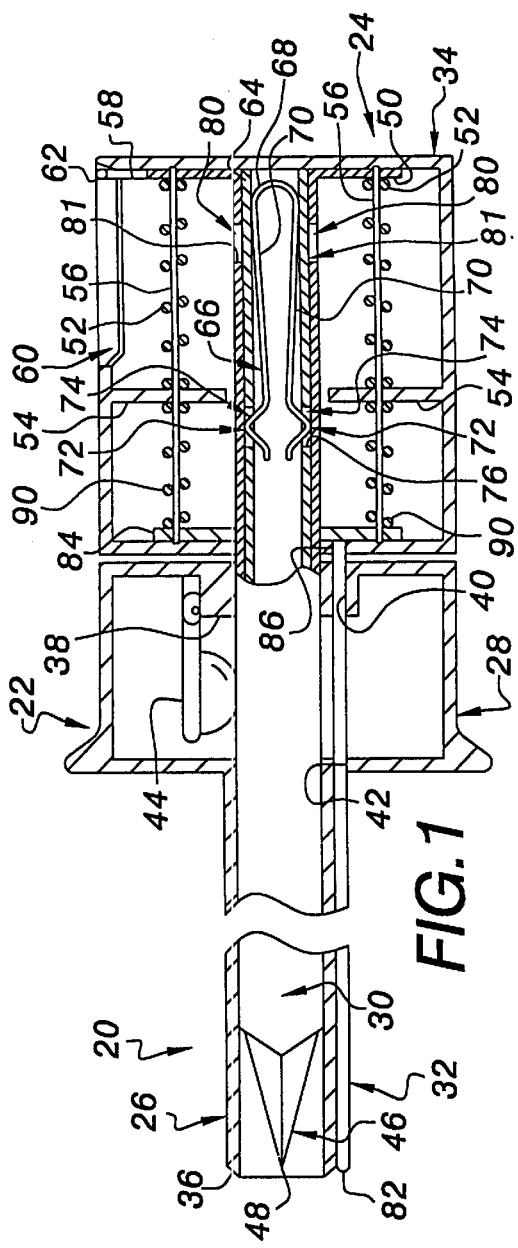
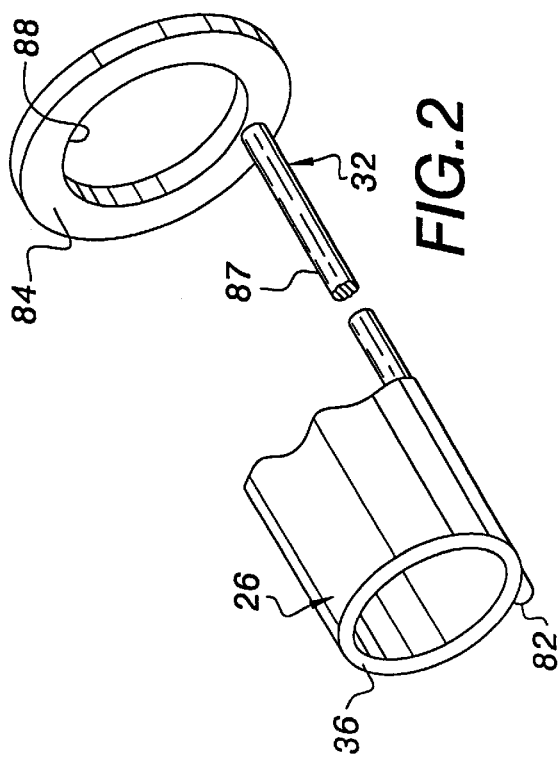
FIG. 2
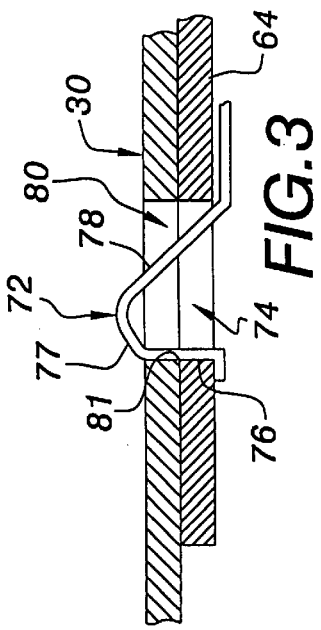
FIG. 3
FIG. 1

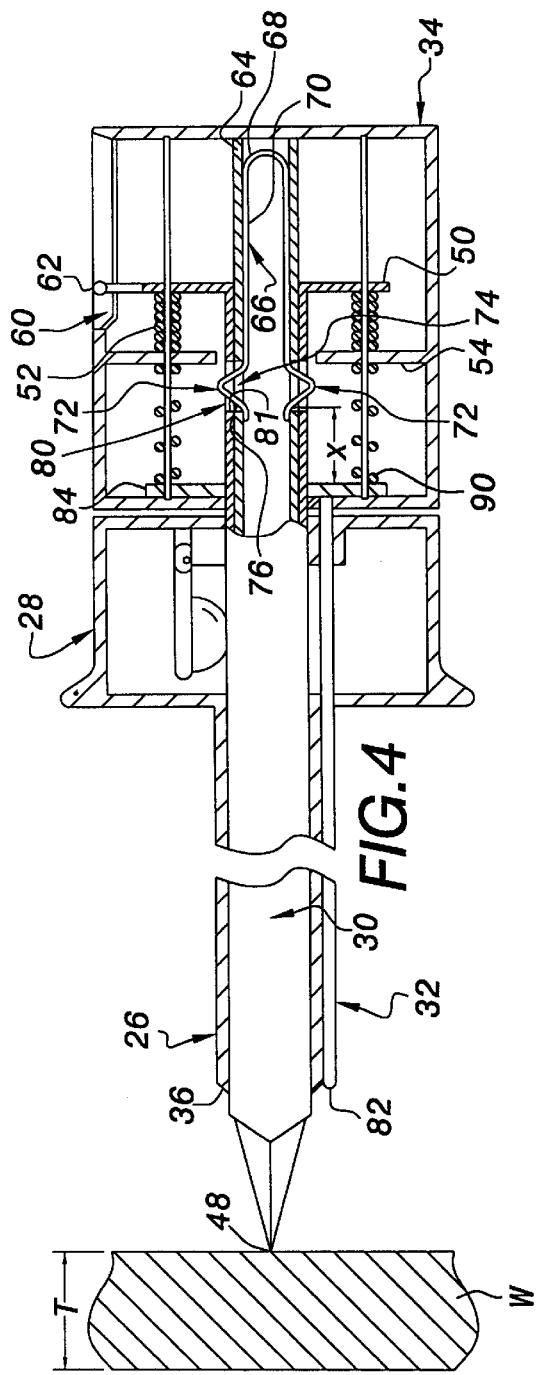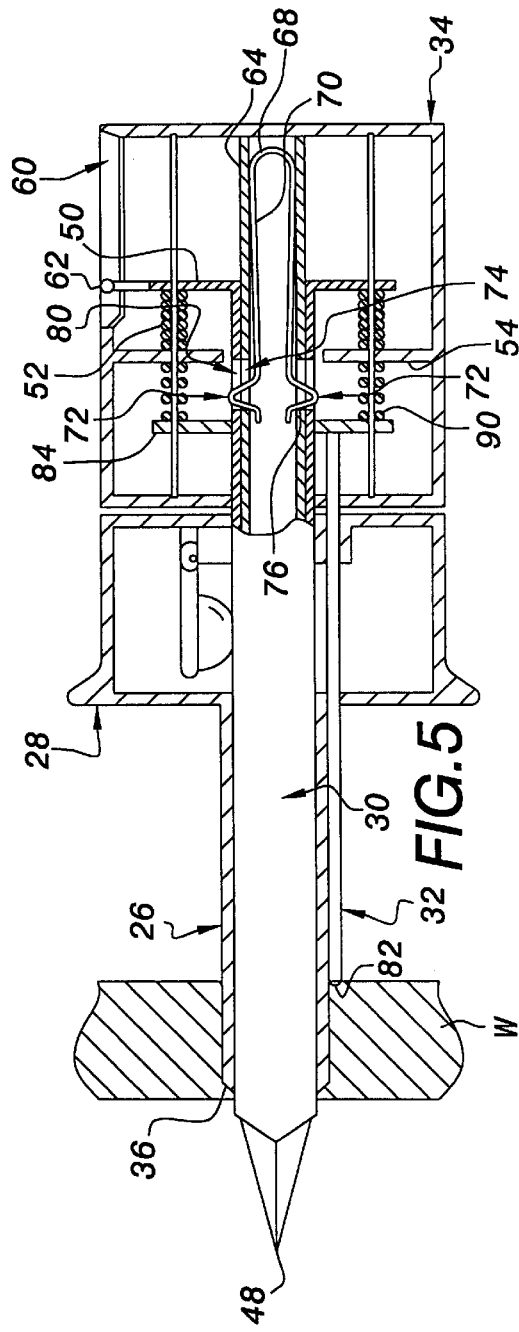

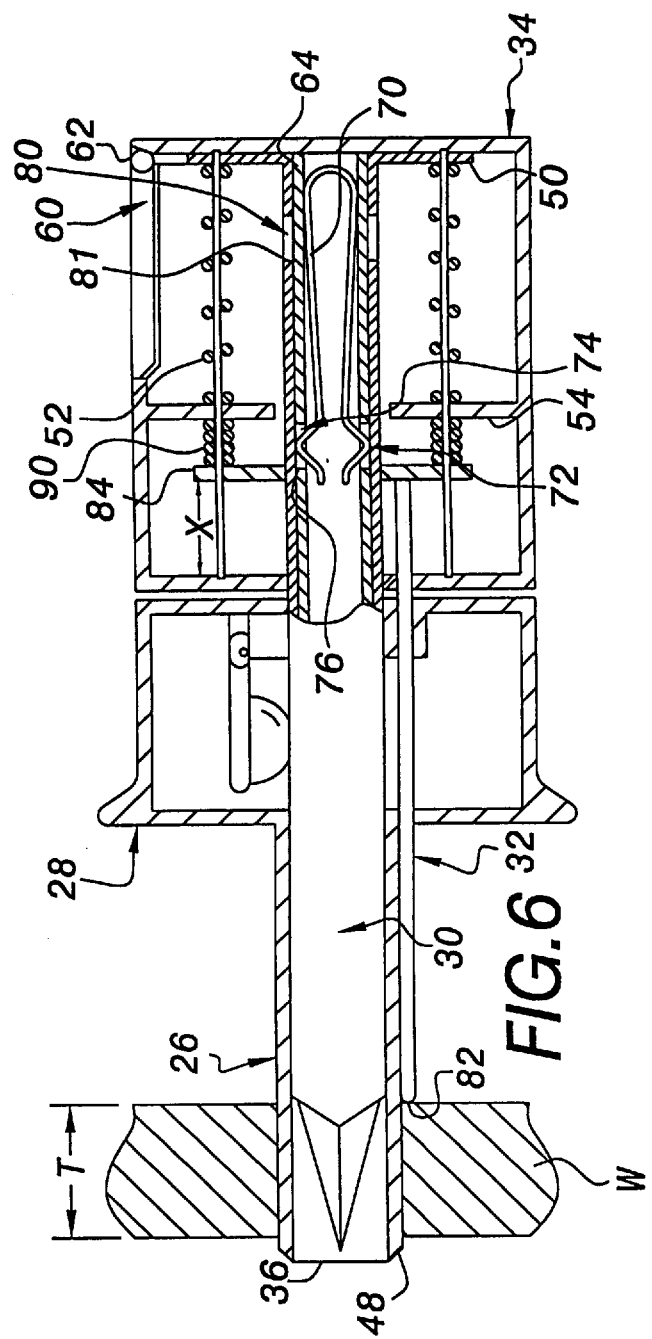

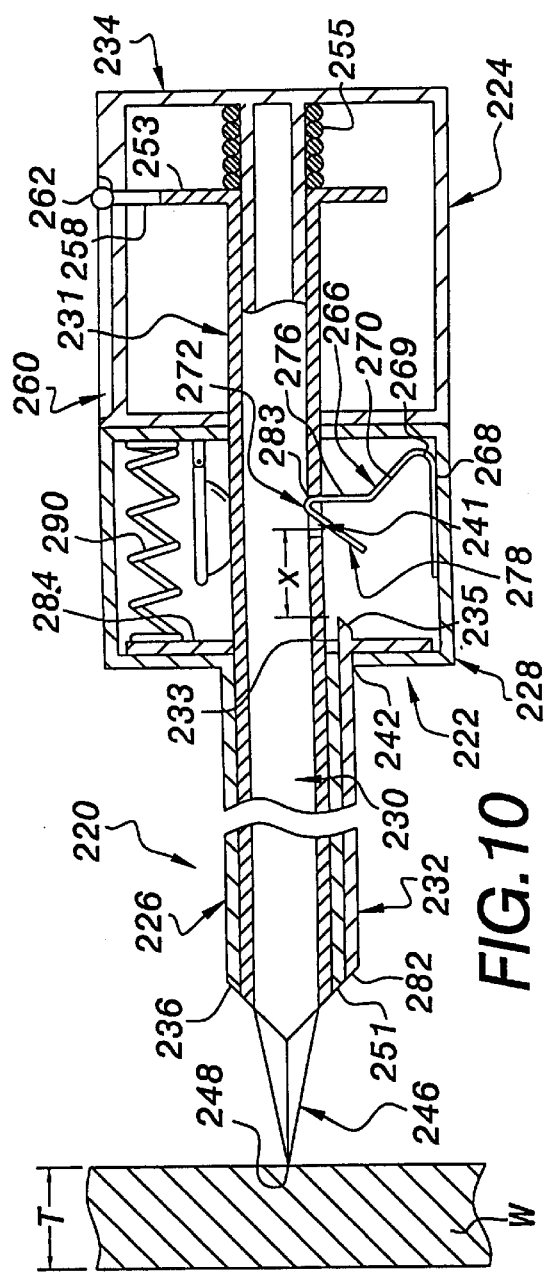
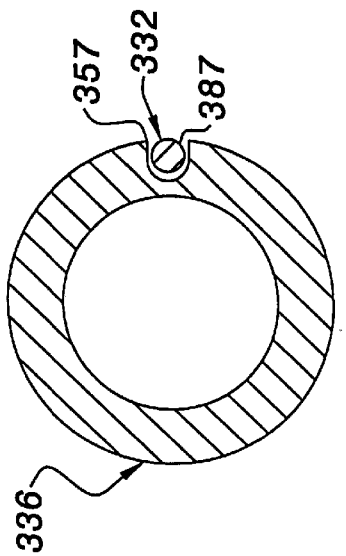
FIG.10
FIG.11

SAFETY PENETRATING INSTRUMENT WITH PENETRATING MEMBER PROTECTED AFTER PENETRATION TO PREDETERMINED DEPTH

BACKGROUND OF THE INVENTION

1. Field of the Invention

The present invention pertains to safety penetrating instruments and, more particularly, to safety penetrating instruments for use in forming portals for establishing communication with anatomical cavities wherein tissue and organ structures are protected from the tips of the penetrating members and to methods of penetrating anatomical cavity walls with safety penetrating instruments.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or least invasive, surgery to establish an endoscopic portal for many various procedures, such as laparoscopic procedures in the abdominal cavity. Such penetrating instruments typically include a cannula or portal sleeve and a penetrating member disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring biased to protrude beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While protruding safety penetrating instruments have been well received, there is room for improvement in reducing the force required to penetrate the cavity wall which necessarily includes the force required to overcome the spring bias on the safety member as well as the resistance of the cavity wall and insuring that the safety member protrudes which normally requires increasing the spring bias on the safety member and, thus, the force to penetrate. Retracting safety penetrating instruments have the disadvantages of requiring relatively complex mechanisms to hold the penetrating member in an extended position during penetration and to release the penetrating member for retraction and, concomitantly, not retracting sufficiently quickly and reliably.

SUMMARY OF THE INVENTION

Accordingly, it is a primary object of the present invention to improve safety penetrating instruments and methods therefor while overcoming the above disadvantages.

Another object of the present invention is to cause a safety penetrating instrument to move to a protected state upon penetration into tissue to a predetermined depth.

A further object of the present invention is to trigger either retraction of a penetrating member or protrusion of a safety member or both after a safety penetrating instrument has penetrated a predetermined distance into a cavity wall.

An additional object of the present invention is to sense the depth of penetration of a safety penetrating instrument into a cavity wall and trigger the safety penetrating instrument to move to a protected state.

The present invention has as another object a method of safely introducing a cannula into an anatomical cavity including the steps of estimating the thickness of the cavity wall, penetrating the cavity wall with a safety penetrating instrument and moving the safety penetrating instrument to a protected state upon penetration into the cavity wall a distance corresponding to the estimated thickness.

Another object of the present invention is to provide a safety penetrating instrument having a trigger member movable a predetermined proximal distance during penetration of an anatomical cavity wall to trigger retraction of a penetrating member and/or protrusion of a safety member.

An additional object of the present invention is to provide a safety penetrating instrument having a trigger member movable proximally a predetermined distance during penetration of an anatomical cavity wall to trigger movement of the safety penetrating instrument to a protected state with the predetermined proximal distance corresponding to the thickness of the cavity wall so that movement to the protected state occurs as soon as penetration into the anatomical cavity has been achieved.

A still further object of the present invention is to provide a safety penetrating instrument having a trigger member movable proximally relative to a cannula a predetermined distance corresponding to a thickness of an anatomical cavity wall to be penetrated for triggering retraction of a penetrating member and/or protrusion of a safety member as soon as a distal end of the cannula has been introduced in the anatomical cavity.

It is also an object of the present invention to provide a method of penetrating an anatomical cavity wall with a safety penetrating instrument wherein predetermined proximal movement of a trigger member of the safety penetrating instrument is selected in accordance with the estimated thickness of the cavity wall to trigger the safety penetrating instrument to move to a protected state as soon as a distal end of a cannula has been introduced in the anatomical cavity.

Some of the advantages of the present invention are that safe penetration is achieved without complex mechanisms while reducing the force required to penetrate a cavity wall, that the safety penetrating instrument can be used for introducing portal sleeves for accommodating passage of instruments therethrough for performing endoscopic procedures, needles for passage of fluids through the instrument and catheters, that the safety and efficacy of safety penetrating instruments can be enhanced, that retraction of the penetrating member can be assured immediately upon completion of penetration, that a safety penetrating instrument can optimally be selected for use in accordance with the estimated or known thickness of an anatomical cavity wall to be penetrated, and that the safety penetrating instrument of the present invention can be inexpensively manufactured with minimum components to reduce cost, facilitate sterilization for re-use and allow economical, single-patient use.

These and other objects, advantages and benefits are realized with the present invention as characterized in a safety penetrating instrument including a cannula having a distal end for being introduced in an anatomical cavity, a proximal end and a lumen between the distal and proximal cannula ends, a penetrating member disposed in the lumen of the cannula and having a distal end for penetrating an anatomical cavity wall, protection means for placing the safety penetrating instrument in a protected state where the distal end of the penetrating member is protected and not exposed and trigger means for triggering the protection means to place the safety penetrating instrument in the protected state. The trigger means is movable proximally a predetermined distance during penetration of the anatomical cavity wall to trigger the protection means to place the safety penetrating instrument in the protected state whereby, when the predetermined proximal distance corresponds to the thickness of the anatomical cavity wall, the safety penetrating instrument will be placed in the protected state when the cannula distal end enters the anatomical cavity.

A method of forming a portal in an anatomical cavity wall according to the present invention is generally characterized by the steps of penetrating the anatomical cavity wall with a safety penetrating instrument having a protective state where a penetrating member of the instrument is protected and triggering the safety penetrating instrument to move to the protective state when a trigger member of the safety penetrating instrument has moved a predetermined proximal distance corresponding to the thickness of the anatomical cavity wall.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 1 is a broken side view, partly in section, of a safety penetrating instrument according to the present invention.

FIG. 2 is a broken side view, partly in section, of the trigger member of the safety penetrating instrument of FIG. 1.

FIG. 3 is an enlarged, broken section of the slot and latch arrangement for the safety penetrating instrument of FIG. 1.

FIG. 4 is a broken side view, partly in section, of the safety penetrating instrument of FIG. 1 just prior to penetration of an anatomical cavity wall.

FIG. 5 is a broken side view, partly in section, of the safety penetrating instrument of FIG. 1 during penetration of the anatomical cavity wall.

FIG. 6 is a broken side view, partly in section, of the safety penetrating instrument of FIG. 1 upon introduction in the anatomical cavity.

FIG. 10 is a broken side view, partly in section, of a further embodiment of a safety penetrating instrument according to the present invention.

FIG. 11 is a sectional view of an alternative arrangement for the trigger member of the safety penetrating instruments according to the present invention.

DESCRIPTION OF THE PREFERRED EMBODIMENTS

Figure 7:
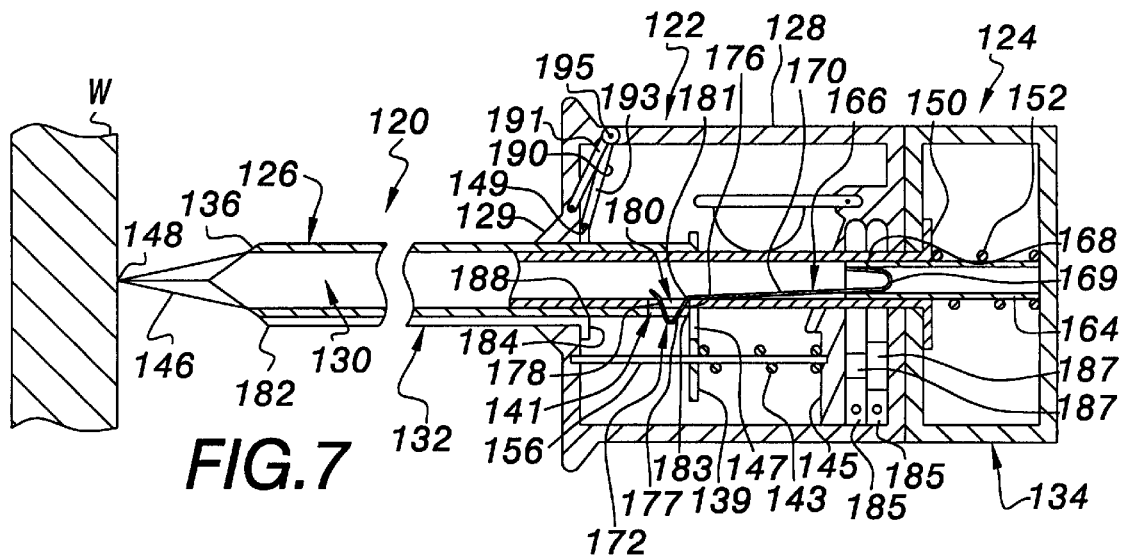
FIG. 7 is a broken side view, partly in section, of another embodiment of a safety penetrating instrument according to the present invention.

The safety penetrating instrument of the present invention is described hereinafter for use as an instrument for inserting a portal sleeve through a wall of an anatomical cavity to form a port for the introduction of various surgical and diagnostic instruments into the cavity during endoscopic procedures, such as laparoscopy. It is understood, however, that the safety penetrating instrument of the present invention can be used for safe penetration or introduction into anatomical cavities of needles with fluid flow therethrough and catheters as well as for other instruments engaging tissue during surgical or diagnostic procedures. Accordingly, the cannula or outer tubular member of the safety penetrating instrument can be a portal sleeve, a needle, a catheter or a tubular component of a medical instrument.

A safety penetrating instrument 20 according to the present invention, as shown in FIG. 1, is formed of a portal unit 22 and a penetrating unit 24. The portal unit 22 includes a cannula in the form of an elongate portal sleeve 26 and a housing 28 mounting a proximal end of portal sleeve 26. The penetrating unit 24 includes an elongate penetrating member 30, shown as a trocar, disposed in portal sleeve 26, a trigger member 32 disposed along side the portal sleeve 26 and a hub 34 mounting proximal ends of the penetrating member and the trigger member. The hub 34 can be latched to the housing 28 with the use of any suitable releasable mechanism, such as detents operated by buttons, allowing the hub to be removed from the housing withdrawing the penetrating member and the trigger member from the portal sleeve.

The portal unit 22 can be made of any desirable, medical grade materials depending on procedural use and desirability of being for single patient use or reusable. Portal sleeve 26 is tubular and can be cylindrical or have any other desired configuration in cross-section in accordance with the procedure to be performed and the anatomical cavity to be penetrated. Portal sleeve 26 is preferably made of a substantially cylindrical length of rigid or flexible, transparent or opaque material, such as stainless steel or other medically acceptable plastic or metal material, and defines a lumen for receiving penetrating member 30. Portal sleeve 26 terminates distally at a distal end 36 and proximally at a proximal end secured to a front wall of the housing 28.

The housing 28 can be made of any desirable material and can have any desirable configuration to facilitate grasping by a surgeon and includes an internal, tubular or hollow neck 38 extending distally from a rear wall of the housing. Neck 38 defines a passage through the housing rear wall aligned with the lumen of the portal sleeve 26 to allow passage therethrough by the penetrating member 30. Neck 38 has a radial thickness in a direction transverse or perpendicular to a longitudinal axis of the safety penetrating instrument 20, and a channel 40 is formed in the thickness of neck 38. As shown in FIG. 1, channel 40 extends longitudinally along neck 38 and through the housing rear wall parallel or substantially parallel with the longitudinal axis. An aperture 42 in the housing front wall is longitudinally aligned with the channel 40 to allow passage through the housing by the trigger member 32 as will be explained further below. The housing 28 is preferably constructed to sealingly engage instruments passing therethrough and to include a valve 44 biased to a closed state when no instrument passes through the portal sleeve. A flapper valve 44 is shown; however, any suitable valve construction can be utilized, for example, trumpet or nipple valves.

Penetrating member 30 includes a shaft or body terminating distally at a distal end 46 having a tip or point 48 for penetrating anatomical tissue and proximally at a transverse flange 50 disposed in hub 34 with the body of the penetrating member passing through an opening in a front wall of the hub longitudinally aligned with the passage of neck 38. The distal end 46 can have any configuration desired by a surgeon for a particular procedure, for example, the pyramidal trocar configuration shown or conical, threaded, multifaceted, open, slanted or needle configurations. The penetrating member 30 can be made of any suitable, medical grade materials and can be made of multiple components such that, for example, the distal end 46 can be made of stainless steel and secured in any conventional manner, such as by threads, to the shaft or body which can be tubular and made of a less expensive material, such as plastic or metal. Retracting members 52 are mounted between flange 50 and transverse internal walls 54 of hub 34 to bias the penetrating member 30 in a proximal direction to a retracted position as shown in FIG. 1 where the tip 48 of the penetrating member is disposed within the portal sleeve 26. As shown, retracting members 52 are formed of helical coil springs 52 mounted in compression between internal walls 54 and flange 50 and around guide rods 56; however, the retracting members can include various other types of springs or other bias devices such as tension springs, torsion springs, leaf springs, rubber, plastic or magnets, for example, and one or more than one retracting member can be provided. A pin 58 extends from flange 50 through a slot 60 in an upper wall of hub 34 to terminate at a handle or knob 62 positioned in an elongate, trough-like recess in the hub upper wall. The slot 60 and the recess extend longitudinally in parallel with the longitudinal axis of the safety penetrating instrument 20 with handle 62 being movable along the slot 60 for use in moving the penetrating member 30 from the retracted position of FIG. 1 to an extended position, shown in FIG. 3, where tip 48 is disposed distally of the portal sleeve distal end 36.

The body of the penetrating member 30 is hollow or tubular or partly hollow or tubular to receive a guide tube 64 extending distally from a rear wall of the hub 34. A locking and releasing mechanism for locking the penetrating member 30 in the extended position and for releasing the penetrating member to move to the retracted position is disposed in guide tube 64 and includes a latch or locking spring 66 made of a strip of resilient material formed to have a curved or semi-circular base 68 secured to or supported by a wall of guide tube 64 or structure within the guide tube and a pair of arms 70 angled outwardly from opposing ends of base 68. Arms 70 extend from base 68 distally in a direction away from the longitudinal axis of the safety penetrating instrument and carry protruding latches 72 extending through opposed slots 74 in the guide tube 64. As shown in FIG. 3, latches 72 are formed of distal latching surfaces 76 disposed transverse to the longitudinal axis and angled surfaces 77 curving to sloping proximal surfaces 78. A pair of opposed slots 80 in the penetrating member body are aligned with slots 74 and with latches 72 when the penetrating member is moved to the extended position, and slots 80 have distal edges 81 for engaging latching surfaces 76 to lock the penetrating member in the extended position.

As shown in FIGS. 1 and 2, trigger member 32 terminates distally at a distal end 82 and proximally at a transverse trigger flange 84 disposed in hub 34 with the trigger member passing through aperture 42 and channel 40 of housing 28 and an aperture 86 in the front wall of hub 34 aligned with channel 40. The trigger member 32 can be arranged in the instrument 20 in many various ways to permit proximal movement of the trigger flange during penetration of an anatomical cavity wall. The trigger member 32 can be made of multiple parts and can have any desirable configuration in cross-section, including cylindrical or rod-like configurations as well as flat configurations, to couple distal end 82 with flange 84 to produce longitudinal proximal movement of flange 84 in response to proximal movement of distal end 82. For example, the trigger member can be formed of a rod 87 separate from flange 84 with the rod 87 having a proximal end exposed proximally of channel 40 so as to be received in aperture 86 when the portal and penetrating units are assembled. In this manner, rod 87 can remain in the portal unit when the penetrating unit is withdrawn to facilitate sealing of housing 28. As shown in FIGS. 1 and 2, trigger member 32 extends along side an external surface of portal sleeve 26 and has an elongate, cylindrical, rod or probe-like configuration between distal end 82 and flange 84. The trigger member 32 is shown as being closely adjacent the portal sleeve external surface with minimal gap or space therebetween while still allowing longitudinal movement of the trigger member relative to the portal sleeve; however, the location of apertures 42 and 86 and channel 40 can be varied from that shown to allow the trigger member to be laterally spaced from the portal sleeve in a direction transverse to the instrument longitudinal axis. Flange 84 is disposed in hub 34 between the front wall thereof and internal wall 54 and has an opening therein allowing passage therethrough of the penetrating member 30. An edge 88 along the flange opening is disposed along an outer or external surface of the penetrating member body for engaging latches 72 to release the penetrating member 30 to move to the retracted position in response to predetermined proximal movement of flange 84 as explained further below. Bias members 90 are mounted between hub internal wall 54 and flange 84 to bias the trigger member distally to a rest position with flange 84 in abutment with the hub forward wall and with trigger distal end 82 aligned or substantially aligned with portal sleeve distal end 36. Helical coil springs 90 mounted in compression around guide rods and between the hub internal walls 54 and flange 84 are shown as the bias members; however, the bias members can include various other types of springs as well as other types of bias devices as previously discussed for retracting members 52. As with retracting members 52, one or more than one bias member 90 can be provided in the safety penetrating instrument 20.

Hub 34 can be made of any desirable medical grade material and can have any desired configuration in cross-section to facilitate grasping of the hub and the housing by a surgeon with one hand. The hub 34 can be removed from the housing 28 allowing the penetrating member 30 and the trigger member 32 to be withdrawn from the portal sleeve 26 leaving the portal sleeve in place.

In use, the safety penetrating instrument 20 will normally be provided in the condition illustrated in FIG. 1 with the penetrating member 30 in the retracted position where the tip 48 of the penetrating member is disposed proximally of the distal end 36 of the portal sleeve to be disposed within the portal sleeve in a safe protected position. With the penetrating member in the retracted position, flange 50 will be biased in abutment with the rear wall of hub 34, and handle 62 will be disposed at a proximal end of slot 60. With the safety penetrating instrument 20 provided in the condition illustrated in FIG. 1, trigger member 32 will be in the rest position with flange 84 biased in abutment with the front wall of hub 34 and trigger member distal end 82 aligned or substantially aligned with portal sleeve distal end 36. Prior to commencing penetration of an anatomical cavity wall W, handle 62 is grasped and manually moved distally along slot 60 until slots 80 in the body of the penetrating member 30 are aligned with latches 72. Once slots 80 are aligned with latches 72, arms 70 will spring outwardly in a direction away from the longitudinal axis of the instrument to the normal position for the locking spring 66 illustrated in FIG. 4 causing latches 72 to protrude through slots 80. At this time, distal latching surfaces 76 will engage edges 81 of the penetrating member body, and the penetrating member 30 will be locked in the extended position with the tip 48 disposed distally of the portal sleeve distal end 36. With the penetrating member 30 locked in the extended position by latches 72, the trigger member 32 will remain in the rest position with distal end 82 aligned or substantially aligned with portal sleeve distal end 36.

The safety penetrating instrument 20 is now ready to be utilized to penetrate an anatomical cavity wall W having a thickness T corresponding to the predetermined distance X that the flange 84 must be moved proximally to release latches 72 and trigger retraction of the penetrating member. The thickness T of the anatomical cavity wall can be estimated by the surgeon prior to commencing penetration in accordance with conventional techniques such as, for example, by grasping or pinching the tissue of the cavity wall between the thumb and forefinger in the manner of a "pinch" test.

During penetration of the anatomical cavity wall W, the penetrating member 30 and the portal sleeve 26 are moved together through the tissue, the penetrating member 30 remaining locked in the extended position. The trigger member 32 is moved proximally relative to the portal sleeve 26 and the penetrating member 30 against the distal bias of bias members 90 due to contact of the trigger member distal end 82 with the anatomical cavity wall W as shown in FIG. 5. Accordingly, the trigger rod 87 acts as a sensing rod to sense the thickness of the cavity wall and to obtain predetermined proximal movement of trigger flange 84 in accordance with the sensed thickness. Movement of the trigger member proximally causes proximal movement of flange 84 and flange edge 88 along penetrating member 30. Once flange 84 has moved the predetermined proximal distance X, the flange edge 88 will engage angled surfaces 77 of latches 72 causing arms 70 to be moved inwardly in the direction of the instrument longitudinal axis. Movement of arms 70 inwardly in the direction of the longitudinal axis causes distal latching surfaces 76 to be disengaged from the edges 81 on the penetrating member body with angled surfaces 77 allowing the penetrating member body to move therepast. Accordingly, retracting members 52 will move the penetrating member 30 to the retracted position where tip 48 is disposed proximally of portal sleeve distal end 36 as shown in FIG. 6. The hub 34 can then be withdrawn from the housing 28 allowing the portal sleeve to remain in place for conducting various procedures via the lumen of the portal sleeve.

By providing the predetermined proximal distance X to be in accordance with the thickness T of the anatomical wall W, retraction of the penetrating member 30 is ensured as soon as the portal sleeve distal end 36 has been introduced in the anatomical cavity. By providing a variety of safety penetrating instruments with different predetermined proximal distances X, a safety penetrating instrument can be optimally selected for use in penetrating a particular known or estimated thickness of anatomical tissue to ensure retraction of the penetrating member immediately upon introduction of the portal sleeve in the anatomical cavity. The predetermined proximal distance that flange 84 must be moved proximally prior to triggering retraction of the penetrating member can be indicated on the instrument by way of any suitable indicia, and safety penetrating instruments can be designed to have adjustable proximal distances X to permit a single safety penetrating instrument to be triggered at various penetration depths.

Although the trigger member distal end 82 is illustrated herein as being aligned with the portal sleeve distal end 36 in the rest position for the trigger member, it will be appreciated that the trigger member distal end 82 can be disposed distally of or proximally of the portal sleeve distal end 36 in the rest position. Where the trigger member distal end 82 is aligned with the portal sleeve distal end 36, the surgeon need only select a safety penetrating instrument having a trigger member movable a predetermined proximal distance equal or substantially equal to the thickness of the anatomical cavity wall. When the thickness of the anatomical cavity wall is greater than the proximal distance X of a specific safety penetrating instrument, the trigger rod 87 can be replaced with a shorter trigger rod to cause triggered retraction after an increased penetration depth; and, similarly, when the thickness of the anatomical cavity wall is less than the proximal distance X, the trigger rod 87 can be replaced with a longer trigger rod. Where the trigger member distal end 82 is disposed distally of the portal sleeve distal end 36 in the rest position, the surgeon can select a safety penetrating instrument having a trigger member movable a predetermined proximal distance equal or substantially equal to the thickness of the anatomical wall plus the distance that the distal end 82 protrudes beyond the distal end 36. Where the trigger member distal end 82 is disposed proximally of the portal sleeve distal end 36, the surgeon can select a safety penetrating instrument having a trigger member movable a predetermined proximal distance equal or substantially equal to the thickness of the anatomical wall less the distance that the distal end 82 is disposed proximally of the distal end 36.

Although the trigger member 32 is disclosed herein along side of and externally of the portal sleeve 26, it will be appreciated that the trigger member can be disposed within the portal sleeve, along side the penetrating member, within the penetrating member or around the penetrating member, for example, and that the trigger member need not pass through the chamber formed in housing 28.

The components of the safety penetrating instrument of the present invention can be made of any suitable, medical grade materials to permit sterilization for reuse or for single patient use. The components can be made of multiple parts of various configurations and materials to reduce cost. The portal unit can have various valves, stop cocks and seals in the housing to control fluid flow therethrough and various adapters to adjust to the size of the instruments inserted through the portal unit. The trigger member can be part of the portal unit or the penetrating unit allowing the trigger member to remain in place with the portal unit or to be withdrawn with the penetrating unit.

With the safety penetrating instrument of the present invention, retraction of the penetrating member can be confirmed by movement of handle 62 proximally along slot 60 and can be felt by the surgeon to provide both visual and tactile confirmation of penetration.

The locking and releasing mechanism requires only a latch for locking the penetrating member in the extended position and a trigger member for releasing the latch upon movement of the trigger member the predetermined proximal distance. It will be appreciated that various mechanisms can be employed to produce the locking and releasing functions such as, for example, multiple movably or pivotally mounted cams or pawls. It will be appreciated that the locking and releasing mechanisms can be longitudinally positioned along the safety penetrating instrument in many various ways to minimize the length of the housing and/or the hub and, therefore, the overall length of the safety penetrating instrument.

Figure 8:
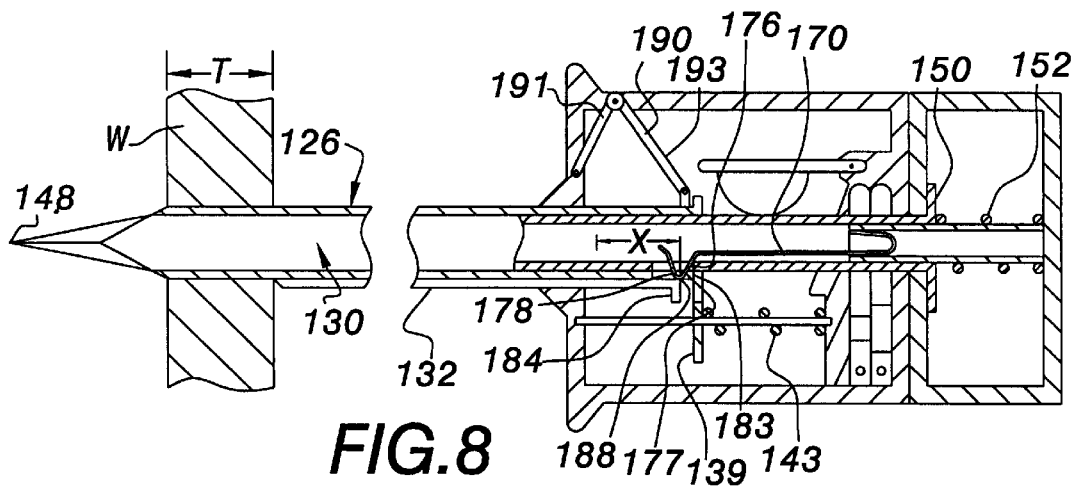
FIG. 8 is a broken side view, partly in section, of the safety penetrating instrument of FIG. 7 during penetration of the anatomical cavity wall.
Figure 9:
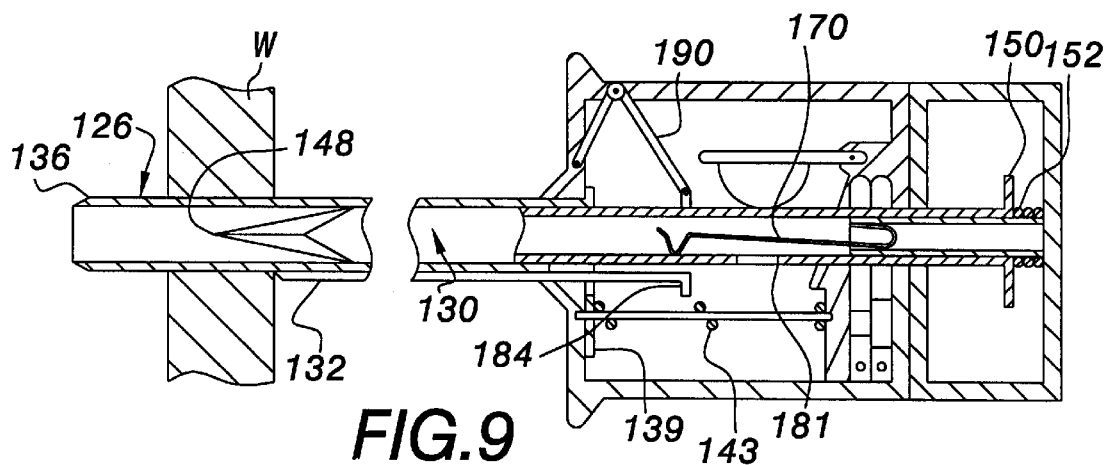
FIG. 9 is a broken side view, partly in section, of the safety penetrating instrument of FIG. 7 upon introduction in the anatomical cavity.

Another embodiment of a safety penetrating instrument 120 according to the present invention is shown in FIGS. 7, 8 and 9 with the primary difference between safety penetrating instruments 20 and 120 being that, while the penetrating member 30 of safety penetrating instrument 20 is retracted into the portal sleeve after a predetermined depth of penetration to define the protected state for the safety penetrating instrument, safety penetrating instrument 120 causes both protrusion of the portal sleeve and retraction of the penetrating member after a predetermined depth of penetration to define the protected state for the safety penetrating instrument. Portal unit 122 for safety penetrating instrument 120 includes portal sleeve 126, trigger member 132 and housing 128 mounting proximal ends of portal sleeve 126 and trigger member 132. Portal sleeve 126 terminates distally at distal end 136 and proximally at a proximal end disposed in housing 128 with the portal sleeve passing through an opening in a distally tapered nose 129 of the front wall of the housing 128. The portal sleeve 126 has a transverse or radial extension or tab 139 at the proximal end thereof and a slot 141 disposed distally of and in longitudinal alignment with extension 139. An extending member 143 is mounted between extension 139 and an internal wall 145 of housing 128 to bias the portal sleeve 126 distally from a portal sleeve retracted position to a portal sleeve extended position as will be explained further below. A helical coil spring 143 mounted in compression between extension 139 and internal wall 145 and disposed around guide rod 156 extending between the front wall and internal wall 145 of housing 128 is shown for the extending member; however, the extending member 143 can include various other types of springs or other bias devices as described previously above. Depending on the arrangement of extension 139 and trigger flange 184, an aperture or notch 147 can be provided in extension 139 to allow movement of extension 139 distally past trigger flange 184 when the portal sleeve is moved from the portal sleeve retracted position to the portal sleeve extended position.

Trigger member 132 is disposed along side portal sleeve 126 and terminates distally at a distal end 182 and proximally at a transverse trigger flange or nub 184 disposed in housing 128 with the trigger member passing through the opening in nose 129. Trigger flange 184 is disposed in housing 128 between the front wall thereof and extension 139 and is coupled to a bias member 190 via a partial circular stirrup terminating at a joint 149 connected to bias member 190. Trigger flange 184 has an edge 188 along the external surface of the portal sleeve 126 for engaging latch 172 and, accordingly, is in longitudinal alignment with slot 141. Trigger flange 184 and extension 139 can be arranged in housing 128 in many various ways to allow distal movement of extension 139 past the trigger flange 184 with or without the notch or aperture 147. A pair of pivotally connected legs 191 and 193 are shown for bias member 190; however, bias member 190 can include various springs as well as other types of bias devices as previously explained above. Leg 191 is connected between the front wall of housing 128 and a pivot, joint or hinge 195 disposed along a side wall of housing 128. Leg 193 is pivotally connected at joint 195 and at joint, pivot or hinge 149. Leg 193 is biased toward leg 191, i.e. clockwise looking at FIG. 7, to bias the trigger member 132 distally to a rest position with trigger flange 184 in abutment with the housing front wall and with trigger distal end 182 aligned or substantially aligned with portal sleeve distal end 136 when the portal sleeve is locked in the portal sleeve retracted position as illustrated in FIG. 7. Leg 193 can be biased toward leg 191 in many various ways such as a torsion spring connected to the housing 128 and the leg 193 at joint 195. Extension 139 can be coupled with a handle such as handle 62 for movement along a slot such as slot 60 in a side wall of housing 128 for use in moving the portal sleeve 126 from the portal sleeve extended position to the portal sleeve retracted position.

Penetrating unit 124 for safety penetrating instrument 120 includes penetrating member 130 and hub 134 mounting a proximal end of the penetrating member. Penetrating member 130 terminates distally at distal end 146 having a tip 148 for penetrating anatomical tissue and proximally at a transverse flange 150 disposed in hub 134 with the body of the penetrating member passing through an opening in a rear wall of housing 128 longitudinally aligned with an opening in a front wall of hub 134. The body of the penetrating member 130 is hollow or tubular or partly hollow or tubular to receive guide tube 164 extending distally from a rear wall of hub 134 and a locking and releasing mechanism for locking the portal sleeve 126 in the portal sleeve retracted position and the penetrating member 130 in a penetrating member extended position as shown in FIG. 7. A retracting member 152 is mounted between flange 150 and the rear wall of hub 134 to bias the penetrating member 130 in a proximal direction to the penetrating member retracted position where the tip 148 of the penetrating member is disposed within the portal sleeve 126. As shown, retracting member 152 is formed of a helical coil spring 152 disposed around guide tube 164; however, the retracting member 152 can include various other types of springs or other bias devices as previously discussed above. Flange 150 can be coupled with a handle such as handle 62 movable along a slot such as slot 60 disposed in a side wall of hub 134 for moving the penetrating member 130 from the penetrating member retracted position to the penetrating member extended position where tip 148 is disposed distally of the portal sleeve distal end 136 with the portal sleeve in the portal sleeve retracted position.

The locking and releasing mechanism for safety penetrating instrument 120 includes a latch or locking spring 166 having a substantially flat base 168 secured to or supported by a wall of guide tube 164 or structure within the guide tube and a bend 169 joining base 168 with an arm 170 angled outwardly from base 168. Arm 170 extends distally in a direction away from a longitudinal axis of the safety penetrating instrument 120 and carries a protruding latch 172. Latch 172 is formed of a proximal latching surface 176 disposed transverse to the longitudinal axis and an angled surface 177 curving to a sloping distal surface 178. A slot 180 is disposed in the penetrating member body for alignment with slot 141 when the portal sleeve is in the portal sleeve retracted position and the penetrating member is in the penetrating member extended position. Slots 180 and 141 have proximal edges 181 and 183, respectively, for engaging proximal latching surface 176 to lock the penetrating member 130 in the penetrating member extended position and the portal sleeve 126 in the portal sleeve retracted position as shown in FIG. 7.

A pair of adjustment plates 185 are disposed in housing 128 between internal wall 145 and the rear wall thereof to be disposed laterally of the penetrating member body when the penetrating unit 124 is assembled with the portal unit 122. Each of the adjustment plates 185 has a different sized opening 187, smaller in size than the opening in the rear wall of housing 128, with longitudinal axes of the openings 187 disposed parallel with the longitudinal axis of the safety penetrating instrument 120. Plates 185 are movable inwardly in the direction of the instrument axis when the penetrating unit is withdrawn from the portal unit to align one of the openings 187 with the opening in the rear wall of housing 128. Accordingly, adjustment plates 185 will form a seal at a proximal end of housing 128 when instruments smaller in size than the opening in the rear wall of housing 128 are inserted in the portal unit. Various mechanisms such as push buttons and handles can be provided for selectively moving plates 185 to align openings 187 with the opening in the housing rear wall, and the plates can be arranged to move linearly or to pivot.

Use of safety penetrating instrument 120 is similar to that previously described for safety penetrating instrument 20. Prior to being utilized to penetrate an anatomical cavity wall W, the portal sleeve 126 will be in the portal sleeve retracted position and the penetrating member 130 will be in the penetrating member extended position as illustrated in FIG. 7 at which time slots 141 and 180 will be in alignment with edges 183 and 181 in engagement with proximal latching surface 176. With the portal sleeve 126 locked in the portal sleeve retracted position and the penetrating member 130 locked in the penetrating member extended position, the tip 148 of the penetrating member will be disposed distally of the portal sleeve distal end 136, and the trigger member 132 will be in the rest position with distal end 182 aligned with or substantially aligned with portal sleeve distal end 136. During penetration of the anatomical cavity wall W, the portal sleeve 126 remains locked in the portal sleeve retracted position and the penetrating member 130 remains locked in the penetrating member extended position. The trigger member 132 is moved proximally against the distal bias of bias member 190 causing movement of flange 184 and flange edge 188 along the portal sleeve 126 as leg 193 pivots, i.e. counterclockwise looking at FIG. 9, away from leg 191. Once flange 184 has moved a predetermined proximal distance X, the flange edge 188 will engage sloping distal surface 178 of latch 172 causing arm 170 to be moved inwardly in the direction of the instrument longitudinal axis as shown in FIG. 8. Movement of arm 170 inwardly in the direction of the instrument longitudinal axis causes proximal latching surface 176 to be disengaged from the edge 183 on the portal sleeve with angled surface 177 allowing the portal sleeve 126 to move distally due to the force of extending member 143. Distal movement of portal sleeve 126 toward the portal sleeve extended position causes further movement of arm 170 inwardly in the direction of the instrument longitudinal axis due to engagement of edge 183 with angled surface 177. Accordingly, proximal latching surface 176 will be disengaged from edge 181 on the penetrating member 130 causing the penetrating member to be moved to the penetrating member retracted position due to the bias of retracting member 152 and the safety penetrating instrument will be in the protected state as shown in FIG. 9. Accordingly, upon movement of trigger flange 184 a predetermined proximal distance X, the portal sleeve 126 will be moved toward the portal sleeve extended position followed immediately by movement of the penetrating member 130 toward the penetrating member retracted position. Movement of the portal sleeve 126 to the portal sleeve extended position causes movement of extension 139 distally past trigger flange 184 since the distal end of the trigger member remains held against the cavity wall W as shown in FIG. 9 to sense the thickness T of the anatomical cavity wall. Where the thickness T corresponds to the predetermined proximal distance X, protrusion of the portal sleeve 126 and retraction of the penetrating member 130 will occur upon entry of the portal sleeve distal end 136 in the anatomical cavity. With the portal sleeve in the portal sleeve extended position and the penetrating member in the penetrating member retracted position, the instrument 120 will be in the protected state illustrated in FIG. 9 with the distal end 136 of the portal sleeve disposed distally of the position of distal end 136 in the portal sleeve retracted position and distally of the position of tip 148 in the penetrating member extended position, and with tip 148 disposed proximally of the position of tip 148 in the penetrating member extended position. If desired, the instrument 120 can be provided in the protected state prior to use and handles and slots as previously described can be utilized to move the penetrating member to the penetrating member extended position and the portal sleeve to the portal sleeve retracted position to align slots 141 and 180 at which time arm 170 will spring back to the normal position for the locking spring illustrated in FIG. 1 to lock the portal sleeve in the portal sleeve retracted position and the penetrating member in the penetrating member extended position.

A further embodiment of a safety penetrating instrument 220 according to the present invention is shown in FIG. 10 with the primary difference between safety penetrating instrument 220 and safety penetrating instruments 20 and 120 being that safety penetrating instrument 220 causes protrusion of a safety member beyond the tip of the penetrating member after a predetermined depth of penetration to define the protected state for the safety penetrating instrument. Portal unit 222 for safety penetrating instrument 220 includes portal sleeve 226, trigger member 232 and housing 228 mounting proximal ends of the portal sleeve and the trigger member. Portal sleeve 226 has a distal end 236 and a proximal end secured to a front wall of housing 228. Trigger member 232 terminates distally at a distal end 282 and proximally at a transverse trigger flange 284 disposed in housing 228 with the trigger member passing through an aperture 242 in the front wall of the housing. Trigger member 232 has a protrusion 233 extending proximally of trigger flange 284 to terminate at an angled edge 235. A bias member 290 including a helical coil spring is mounted between trigger flange 284 and a rear wall of housing 128 to bias the trigger member distally to a rest position with flange 284 in abutment with the housing front wall and with trigger distal end 282 aligned or substantially aligned with portal sleeve distal end 236. Although a helical coil spring is shown as the bias member 90, various other types of springs and other bias devices can be utilized for the bias member as discussed previously above.

A locking and releasing mechanism for locking the safety member in a safety member retracted position and for releasing the safety member to move to a safety member extended position is disposed in housing 228 and includes a latch or locking spring 266 made of a strip of resilient material formed to have a substantially flat base 268 secured to or supported by a wall of housing 128 or structure within the housing and a bend 269 connecting base 268 with an upwardly angled arm 270 extending distally from bend 269 in the direction of a longitudinal axis of the safety penetrating instrument. Arm 270 carries a protruding latch 272 formed of a proximal latching surface 276 disposed transverse to the longitudinal axis and an angled or sloping distal surface 278 joined to proximal latching surface 276 with the angle or slope of the distal surface 278 being the same or substantially the same as the angle of edge 235.

Penetrating unit 224 for safety penetrating instrument 220 includes penetrating member 230, safety member 231 and hub 234 mounting proximal ends of the safety member and the penetrating member. The penetrating member 230 terminates distally at distal end 246 having tip 248 for penetrating anatomical tissue and proximally at a proximal end secured to a rear wall of hub 234. Safety member 231 terminates distally at a distal end 251 and proximally at a transverse flange 253 disposed in hub 234 with a body coupling distal end 251 with flange 253, the body of the safety member passing through aligned openings in a rear wall of housing 228 and a front wall of hub 234. The safety member distal end 251 can have any desirable configuration to protect tissue or organ structure, and the body of the safety member can have any desirable configuration to couple distal end 251 with flange 253. As shown, safety member 231 is in the nature of a shield having a tubular configuration with a lumen to receive penetrating member 230; however, the safety member can have various other configurations including various shield and probe configurations. Although the safety member 231 is concentrically disposed around the penetrating member 230 to be received within the portal sleeve 226, the safety member can be arranged in many various ways including around the penetrating member, within the penetrating member or alongside the penetrating member. An extending member 255 is mounted between flange 253 and the rear wall of hub 234 for moving the safety member from the safety member retracted position to the safety member extended position and includes a helical coil spring disposed around the penetrating member 230. A pin 258 extends from flange 253 through a slot 260 in an upper wall of hub 234 to terminate at a handle 262 for use in moving the safety member from the safety member extended position to the safety member retracted position illustrated in FIG. 10 where tip 248 is disposed distally of the safety member distal end 251. A slot 241 is disposed in the body of the safety member to be disposed in housing 228 and has a proximal edge 283 for engagement with proximal latching surface 276 to lock the safety member in the safety member retracted position.

Use of safety penetrating instrument 220 is similar to that previously described. The safety penetrating instrument 220 will normally be provided in the protected state with the safety member 231 in the safety member extended position protecting tip 248. With the safety member in the safety member extended position, safety member distal end 251 will be disposed distally of tip 248, and handle 262 will be disposed toward a distal end of slot 260. When it is desired to penetrate an anatomical cavity wall W utilizing the safety penetrating instrument 220, handle 262 is moved proximally to align slot 241 with latch 272 causing arm 270 to spring back to the normal position illustrated in FIG. 10 at which time edge 283 will be in engagement with proximal latching surface 276 to lock the safety member in the safety member retracted position. The instrument 220 will now be ready for use in penetrating an anatomical cavity wall W and will be in the position illustrated in FIG. 10 with the trigger member in the rest position with distal end 282 aligned or substantially aligned with portal sleeve distal end 236 and the safety member in the safety member retracted position with distal end 251 aligned or substantially aligned with the portal sleeve distal end 236. During penetration of the anatomical cavity wall W, the trigger member 232 is moved proximally against the distal bias of bias member 290 causing proximal movement of flange 284 and edge 235. Once edge 235 has moved proximally a predetermined distance X, edge 235 will engage angled surface 278 of latch 272 causing arm 270 to be moved or cammed in a direction away from the instrument longitudinal axis and toward base 268. Movement of arm 270 toward base 268 outwardly causes proximal latching surface 276 to be disengaged from edge 283 causing the safety member 251 to be moved to the safety member extended position due to the bias of extending member 255. Once the safety member 251 has been moved to the safety member extended position, the instrument 220 will be in the protected state with tip 248 of penetrating member 230 disposed within the safety member. By selecting distance X to correspond to the thickness T of wall W, protrusion of the safety member will occur upon entry of the portal sleeve distal end 236 in the anatomical cavity.

FIG. 11 illustrates an alternative arrangement for the trigger member for the safety penetrating instruments according to the present invention. As illustrated in FIG. 11, portal sleeve 326 has a recess 357 formed along an external or peripheral surface thereof with the recess 357 extending into the thickness of the wall of the portal sleeve. Recess 357 is defined by a curved surface corresponding in curvature to the curvature of rod 387 of trigger member 382. Rod 387 is disposed in recess 357 such that a portion of the rod 387 completes the periphery of the portal sleeve 326 along recess 357.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for penetrating an anatomical cavity wall to gain access to an anatomical cavity comprising a cannula having a distal end for introduction in the anatomical cavity, a proximal end for being disposed externally of the anatomical cavity and a lumen between said distal and proximal ends of said cannula;

a penetrating member disposed in said lumen of said cannula and having a distal end for penetrating the anatomical cavity wall;

protection means for placing said safety penetrating instrument in a protected state where said distal end of said penetrating member is in a protected, non-exposed position; and trigger means proximally movable during penetration of the anatomical cavity wall for triggering said protection means to place said safety penetrating instrument in said protected state upon said trigger means moving proximally a predetermined distance whereby, when said predetermined proximal distance corresponds to the thickness of the anatomical cavity wall, said safety penetrating instrument will be placed in said protected state when said portal sleeve distal end enters the anatomical cavity.

2. A safety penetrating instrument as recited in claim 1 wherein said trigger means is disposed along side of said cannula.

3. A safety penetrating instrument as recited in claim 2 wherein said trigger means is disposed externally of said cannula.

4. A safety penetrating instrument as recited in claim 3 and further including means for biasing said trigger means distally to a rest position and for permitting said trigger means to move proximally from said rest position during penetration of the anatomical cavity wall.

5. A safety penetrating instrument as recited in claim 4 wherein said trigger means includes a distal end aligned with said cannula distal end in said rest position.

6. A safety penetrating instrument for penetrating an anatomical cavity wall to gain access to an anatomical cavity comprising
a cannula having a distal end for introduction in the anatomical cavity, a proximal end and a lumen between said distal and proximal ends of said cannula;
a penetrating member disposed in said lumen of said cannula and having a distal end for penetrating the anatomical cavity wall;
retracting means for moving said penetrating member proximally from an extended position where said penetrating member distal end is disposed distally of said cannula distal end to a retracted position where said penetrating member distal end is disposed within said cannula distal end;
locking means for locking said penetrating member in said extended position; and
a trigger member movable a predetermined proximal distance during penetration of the anatomical cavity wall for triggering release of said locking means to permit said retracting means to move said penetrating member from said extended position to said retracted position, said predetermined distance corresponding to the thickness of the anatomical cavity wall to allow said penetrating member to be moved to said retracted position upon introduction of said cannula distal end in the anatomical cavity.

7. A safety penetrating instrument as recited in claim 6 wherein said penetrating member includes a proximal end and said trigger member includes a proximal end and further including a housing for mounting said proximal end of said cannula and a hub for mounting said proximal ends of said penetrating member and said trigger member.

8. A safety penetrating instrument as recited in claim 7 wherein said trigger member extends through said housing to be disposed along side of said cannula.

9. A safety penetrating instrument as recited in claim 8 wherein said penetrating member and said trigger member are removable from said cannula.

10. A safety penetrating instrument as recited in claim 7 wherein said trigger member has a distal end disposed adjacent said distal end of said cannula prior to penetration of the anatomical cavity wall and movable proximally relative to said cannula during penetration of the anatomical cavity wall and said proximal end of said trigger member is coupled with said trigger member distal end for being moved said predetermined distance in response to movement of said trigger member distal end.

11. A safety penetrating instrument as recited in claim 10 wherein said locking means includes a latch for engaging said penetrating member in said extended position.

12. A safety penetrating instrument as recited in claim 11 wherein said trigger member proximal end includes means for engaging said latch upon movement of said trigger member proximal end said predetermined distance to move said latch out of engagement with said penetrating member.

13. A safety penetrating instrument as recited in claim 6 wherein said cannula is moved from a cannula retracted position where said cannula distal end is disposed proximally of the location of said penetrating member distal end in said penetrating member extended position and a cannula extended position where said cannula distal end is disposed distally of the location of said penetrating member distal end in said penetrating member extended position and further including means for moving said cannula from said cannula retracted position to said cannula extended position in response to movement of said trigger member said predetermined distance.

14. A method of forming a portal in the wall of an anatomical cavity comprising the steps of
penetrating the anatomical cavity wall with a penetrating member of a safety penetrating instrument having a protective state where the penetrating member is protected and a trigger member movable proximally a proximal distance corresponding to the thickness of the anatomical cavity wall; and
triggering the safety penetrating instrument to move to the protective state when the trigger member has moved the proximal distance.

15. A method as recited in claim 14 and further comprising the step of contacting the anatomical cavity wall with the trigger member during said penetrating step.

16. A method as recited in claim 14 and further comprising the steps of estimating the thickness of the anatomical cavity wall and selecting a safety penetrating instrument having a proximal distance movement corresponding to the estimated anatomical cavity wall thickness for said penetrating step.

17. A method as recited in claim 14 and further comprising the steps of estimating the thickness of the anatomical cavity wall and adjusting the proximal distance movement of the safety penetrating instrument to correspond to the estimated anatomical wall thickness.

18. A method as recited in claim 14 where the safety penetrating instrument includes a cannula movably receiving the penetrating member and said triggering step includes moving the penetrating member proximally into the cannula.

19. A method as recited in claim 18 wherein said triggering step includes moving the cannula distally.

20. A method as recited in claim 14 wherein the safety penetrating instrument includes a cannula movably receiving the penetrating member and said triggering step includes moving the cannula distally to protrude beyond the penetrating member.

21. A method as recited in claim 14 wherein the safety penetrating instrument includes a cannula receiving the penetrating member and a safety member longitudinally movable relative to the penetrating member and said triggering step includes moving the safety member distally to protrude beyond the penetrating member.

22. A method of penetrating tissue comprising the steps of
penetrating the tissue with the distal end of a penetrating member of a safety penetrating instrument including a cannula receiving the penetrating member and adapted to remain in the tissue after the penetrating member is withdrawn from the cannula; and
triggering the safety penetrating instrument to move the safety penetrating instrument to a protective state where the penetrating member is protected as soon as a trigger member of the safety penetrating instrument has moved proximally a distance corresponding to a desired predetermined depth of penetration by the safety penetrating instrument into the tissue.

23. A method as recited in claim 22 and further comprising the step of sensing the depth of penetration of the safety penetrating instrument into the tissue.

24. A method as recited in claim 23 wherein said triggering step includes retracting the distal end of the penetrating member proximally into the cannula.

25. A method as recited in claim 24 wherein said triggering step includes moving the cannula distally.

26. A method as recited in claim 23 wherein said triggering step includes moving the cannula distally to protrude beyond the distal end of the penetrating member.

27. A method as recited in claim 23 wherein the safety penetrating instrument includes a safety member longitudinally movable relative to the penetrating member and said triggering step includes moving the safety member distally to protrude beyond the distal end of the penetrating member.

* * * * *